(12) United States Patent
Kubota et al.

(10) Patent No.: US 8,962,669 B2
(45) Date of Patent: *Feb. 24, 2015

(54) ANTIMYCOTIC PHARMACEUTICAL COMPOSITION

(75) Inventors: Nobuo Kubota, Yokohama (JP); Hirokazu Kobayashi, Yokohama (JP); Takaaki Masuda, Yokohama (JP)

(73) Assignees: Pola Pharma Inc., Shinagawa-ku, Tokyo (JP); Nihon Nohyaku Co., Ltd., Chuo-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/703,300

(22) PCT Filed: Jun. 10, 2011

(86) PCT No.: PCT/JP2011/063860
§ 371 (c)(1),
(2), (4) Date: Dec. 10, 2012

(87) PCT Pub. No.: WO2011/155640
PCT Pub. Date: Dec. 15, 2011

(65) Prior Publication Data
US 2013/0090365 A1    Apr. 11, 2013

(30) Foreign Application Priority Data

Jun. 11, 2010 (JP) ................. 2010-148255
Jul. 30, 2010 (JP) ................. 2010-181923

(51) Int. Cl.
| | | |
|---|---|---|
| C07D 401/00 | (2006.01) | |
| A61K 31/4178 | (2006.01) | |
| A61K 9/00 | (2006.01) | |
| A61K 9/08 | (2006.01) | |
| A61K 31/385 | (2006.01) | |
| A61K 47/14 | (2006.01) | |
| A61K 47/10 | (2006.01) | |
| A61K 47/22 | (2006.01) | |

(52) U.S. Cl.
CPC ........... *A61K 31/4178* (2013.01); *A61K 9/0014* (2013.01); *A61K 9/08* (2013.01); *A61K 31/385* (2013.01); *A61K 47/14* (2013.01); *A61K 47/10* (2013.01); *A61K 47/22* (2013.01)
USPC ............................ 514/397; 424/404

(58) Field of Classification Search
USPC ............................ 514/397; 424/404
See application file for complete search history.

(56) References Cited

U.S. PATENT DOCUMENTS

| | | |
|---|---|---|
| 8,058,303 B2 | 11/2011 | Miki et al. |
| 8,268,876 B2 | 9/2012 | Miki et al. |
| 2009/0137651 A1 | 5/2009 | Kobayashi et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2012/0014893 A1 | 1/2012 | Kobayashi et al. |
| 2012/0015997 A1 | 1/2012 | Miki et al. |
| 2012/0022120 A1 | 1/2012 | Kobayashi et al. |
| 2012/0149745 A1 | 6/2012 | Kobayashi et al. |
| 2013/0011351 A2 | 1/2013 | Kobayashi et al. |
| 2014/0080882 A1 | 3/2014 | Masuda et al. |

FOREIGN PATENT DOCUMENTS

| | | | |
|---|---|---|---|
| CN | 101137369 A | * | 3/2008 |
| EP | 0 268 460 | | 5/1988 |
| EP | 0715856 A1 | | 6/1996 |
| EP | 2005958 A1 | | 12/2008 |
| EP | 2 025 337 | | 2/2009 |

(Continued)

OTHER PUBLICATIONS

Machine Translation of CN 101137369 (retrieved from EPO: http://translationportal.epo.org/emtp/translate/?ACTION=description-retrieval&COUNTRY=CN&ENGINE=google&FORMAT=docdb&KIND=A&LOCALE=en_EP&NUMBER=101137369&OPS=cn.espacenet.com/ops&SRCLANG=zh&TRGLANG=en (Aug. 27, 2014)).*

(Continued)

*Primary Examiner* — Ernst V Arnold
*Assistant Examiner* — Kyung Sook Chang
(74) *Attorney, Agent, or Firm* — Knobbe, Martens, Olson & Bear LLP

(57) ABSTRACT

An object is to provide a medicament preparation which is excellent in the solubilization stability in relation to a compound represented by the general formula (1) during the storage in a low temperature region and a high temperature region. The present invention resides in a pharmaceutical composition comprising 1) the compound represented by the general formula (1) and/or a salt thereof and 2) a polyhydric alcohol derivative. General formula (1) (In the formula, $R_1$, $R_2$ independently represent hydrogen atom or halogen atom respectively, and at least one of $R_1$, $R_2$ is halogen atom.)

(1)

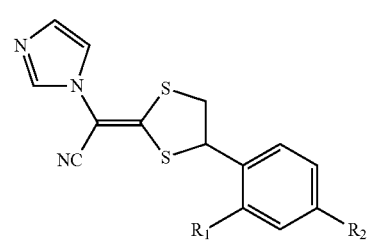

8 Claims, No Drawings

(56) References Cited

FOREIGN PATENT DOCUMENTS

| | | |
|---|---|---|
| EP | 2 191 825 | 6/2010 |
| EP | 2 191 826 | 6/2010 |
| EP | 2 191 827 | 6/2010 |
| JP | 08-245377 | 9/1996 |
| JP | 2002-114680 A | 4/2002 |
| JP | 2002-363070 | 12/2002 |
| JP | 2006-306734 | 11/2006 |
| WO | WO 97/02821 | 1/1997 |
| WO | WO 99/39680 | 8/1999 |
| WO | WO 2004/091521 | 10/2004 |
| WO | WO 2009031643 A1 * | 3/2009 |
| WO | WO 2014/041708 A1 | 3/2014 |
| WO | WO 2014/041825 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

International Search Report dated Oct. 4, 2011 issued to priority international application No. PCT/JP2011/063860.

Niwano et al., "Efficacy of NND-502, a novel imidazole antimycotic agent, in experimental models of *Candida albicans* and *Aspergillus fumigatus* infections," *International Journal of Antimicrobial Agents*, vol. 12, pp. 221-228 (1999).

U.S. Appl. No. 14/263,293, Masuda et al.

* cited by examiner

ANTIMYCOTIC PHARMACEUTICAL COMPOSITION

CROSS-REFERENCE TO RELATED APPLICATIONS

This application is the U.S. National Phase under 35 U.S.C. §371 of International Application PCT/JP2011/063860, filed Jun. 10, 2011, which claims priority to JP 2010-148255, filed Jun. 11, 2010 and JP 2010-181923, filed Jul. 30, 2010.

TECHNICAL FIELD

The present invention relates to a pharmaceutical composition. In particular, the present invention relates to a pharmaceutical composition which is useful as an antimycotic agent.

BACKGROUND ART

Luliconazole is a compound having a structure represented by the general formula (1) ($R_1$=$R_2$=chlorine atom), and it has an excellent antimycotic activity. It is pointed out that luliconazole may be possibly applied to treat the onychomycosis which has been hitherto regarded to be untreatable by means of any external administration as well (see, for example, Patent Document 1). As for the medicament preparation (pharmaceutical preparation) to treat the onychomycosis as described above, it is desired that the content of the compound represented by the general formula (1) is further increased. However, there has been such a situation that the solvent, which can be used to prepare any medicament preparation containing the foregoing compound at a high concentration, is inevitably limited strictly, because of the excellent crystallization performance of the compound. That is, any inconvenience arises in some cases depending on the type of the solvent, for example, such that the crystals are deposited under a low temperature condition, for example, at 5° C. and/or the crystals are deposited upon the application. Additionally, a situation arises such that the stereoisomer such as SE isomer or the like tends to appear in a solution of luliconazole. Only crotamiton, propylene carbonate, and N-methyl-2-pyrrolidone are known as the solvent to avoid the appearance of the stereoisomer as described above (see, for example, Patent Document 2). However, even in the case of the solvent as described above, the blending is sometime limited or restricted on account of the efficacy or medical effect such as the anti-inflammatory effect as originally possessed. It has been desired to develop a novel solvent which replaces the conventional solvent and which is usable for the medicament preparation of luliconazole or the like. In particular, the medical effect is extremely reduced, for example, due to the crystal deposition in the case of a medicament preparation in a form of solution. Therefore, the solubilizing technique is an important factor for preparing or formulating the medicament preparation of luliconazole or the like. Additionally, there is also such a situation that the stereoisomer such as Z isomer should be taken into consideration as well.

Lanoconazole ($R_1$=hydrogen atom, $R_2$=chlorine atom) is also known as a useful antimycotic agent as the compound represented by the general formula (1). However, in the case of this compound, a serious problem also arises in relation to the production technique such that the crystals are deposited during the use in a low temperature region and the content is decreased on account of the storage in a high temperature region.

On the other hand, certain components, which are exemplified, for example, by acylated (poly)ethylene glycol and short chain or middle chain triglycerides such as triacetin and the like, are widely used in the world as solvents or surfactants which are excellent in the solubilizing power (see, for example, Patent Document 3). However, any pharmaceutical medicament preparation is not known, which contains 1) a compound represented by the following general formula (1) and/or a salt thereof and 2) an acylated derivative, an etherified derivative, or an oxolane derivative of a polyhydric alcohol.

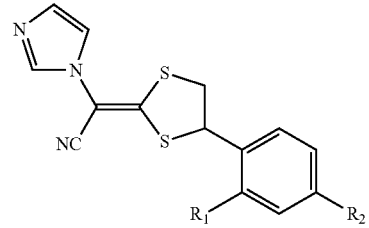

General formula (1)

(wherein, in the formula, $R_1$, $R_2$ independently represent hydrogen atom or halogen atom respectively, and at least one of $R_1$, $R_2$ is halogen atom.)

PATENT DOCUMENTS

Patent Document 1: International Publication No. 2007/102241;
Patent Document 2: International Publication No. 2007/102242;
Patent Document 3: Japanese Patent Application Laid-open No. 08-245377.

SUMMARY OF THE INVENTION

The present invention has been made in the circumstances as described above, an object of which is to provide a medicament preparation or pharmaceutical preparation that is excellent in the solubilization stability in relation to the compound represented by the general formula (1) during the storage in a low temperature region and a high temperature region.

Taking the foregoing circumstances into consideration, the present inventors have diligently performed repeated studies and efforts in order to seek for a component of medicament preparation which is capable of replacing such as N-methyl-2-pyrrolidone and propylene carbonate and which has the action to enhance the solubilization stability during the storage of the compound represented by the general formula (1) in the low temperature region and the high temperature region. As a result, it has been found out that a derivative of polyhydric alcohol has such a characteristic, and the invention has been finally completed. That is, the present invention is as follows.

<1> A pharmaceutical composition comprising: 1) a compound represented by the following general formula (1) and/or a salt thereof and 2) a polyhydric alcohol derivative.

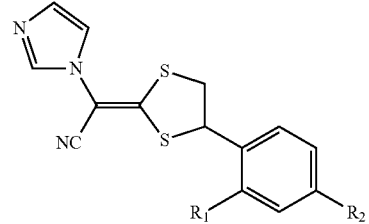

General formula (1)

In the formula, $R_1$, $R_2$ independently represent hydrogen atom or halogen atom respectively, and at least one of $R_1$, $R_2$ is halogen atom.

<2> The pharmaceutical composition as defined in <1>, wherein the compound represented by the general formula (1) is luliconazole and wherein $R_1=R_2=$chlorine atom.

<3> The pharmaceutical composition as defined in <1> or <2>, wherein the polyhydric alcohol derivative is an oxolane derivative represented by the following general formula (2).

General formula (2)

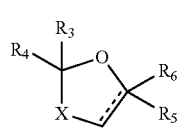

In the formula, $R_3$, $R_4$, $R_5$, $R_6$ independently represent hydrogen atom, oxygen atom, carboxyl group, hydroxyalkyl group having a number of carbon atom or atoms of 1 to 4, or alkyl group having a number of carbon atom or atoms of 1 to 4, $R_3$, $R_4$ and/or $R_5$, $R_6$ may represent the same atom together, X represents carbon atom to which hydrogen atom is bonded or oxygen atom, bond indicated by a broken line may be either present or absent, and $R_6$ is absent when the bond indicated by the broken line is present, provided that propylene carbonate is excluded.

<4> The pharmaceutical composition as defined in <3>, wherein the oxolane derivative represented by the general formula (2) is selected from tetrahydrofuran, 1,3-dioxolane, 2-oxo-1,3-dioxolane, 5-oxotetrahydrofuran-2-carboxylic acid, γ-crotonolactone, and 2,2-dimethyl-1,3-dioxolane-4-methanol.

<5> The pharmaceutical composition as defined in <1> or <2>, wherein the polyhydric alcohol derivative is an acylated compound or an etherified compound of polyhydric alcohol.

<6> The pharmaceutical composition as defined in <5>, wherein the acylated compound of polyhydric alcohol is a triglyceride of short chain or middle chain fatty acid or an ester of short chain or long chain fatty acid and (poly)ethylene glycol.

<7> The pharmaceutical composition as defined in <6>, wherein the triglyceride of short chain or middle chain fatty acid is selected from triacetin, tricaprilin, glycerol trioctanoate, and glycerol tri(caprylate/caprate).

<8> The pharmaceutical composition as defined in <6>, wherein the ester of short chain or long chain fatty acid and (poly)ethylene glycol is selected from ethylene glycol monoacetate, polyethylene glycol monolaurate, and polyethylene glycol monooleate.

<9> The pharmaceutical composition as defined in <5>, wherein the etherified compound of polyhydric alcohol is selected from polyethylene glycol alkyl ether, polyoxyethylene alkyl ether, and polyoxyethylene-polyoxypropylene alkyl ether.

<10> The pharmaceutical composition as defined in <9>, wherein:

the polyethylene glycol alkyl ether is selected from diethylene glycol monoethyl ether, diethylene glycol monobenzyl ether, diethylene glycol diethyl ether, and triethylene glycol dimethyl ether;

the polyoxyethylene alkyl ether is selected from polyoxyethylene lauryl ether and polyoxyethylene cetyl ether; and the polyoxyethylene-polyoxypropylene alkyl ether is polyoxyethylene-polyoxypropylene cetyl ether.

<11> The pharmaceutical composition as defined in any one of <1> to <10>, further comprising hydroxyalkylbenzene.

<12> The pharmaceutical composition as defined in <11>, wherein the hydroxyalkylbenzene is benzyl alcohol.

<13> The pharmaceutical composition as defined in any one of <1> to <12>, further comprising α-hydroxy acid and/or phosphoric acid.

<14> A method for producing a pharmaceutical composition comprising 1) a compound represented by the following general formula (1) and/or a salt thereof, 2) a polyhydric alcohol derivative, and 3) hydroxyalkylbenzene, the method comprising:

mixing hydroxyalkylbenzene as a dissolution auxiliary agent with the compound represented by the general formula (1) and/or the salt thereof; and mixing an obtained mixture with the polyhydric alcohol derivative as a dilution medium.

General formula (1)

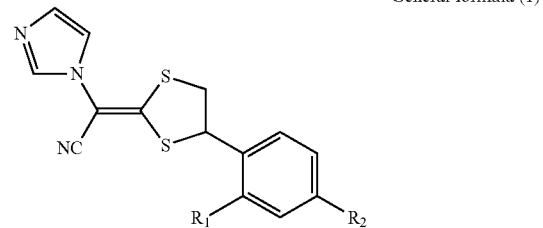

In the formula, $R_1$, $R_2$ independently represent hydrogen atom or halogen atom respectively, and at least one of $R_1$, $R_2$ is halogen atom.

According to the present invention, it is possible to provide the medicament preparation which is excellent in the solubilization stability in relation to the compound represented by the general formula (1) during the storage in the low temperature region and the high temperature region.

DESCRIPTION OF EMBODIMENTS

Next, a preferred embodiment of the present invention will be explained in detail. However, the present invention is not limited to the preferred embodiment described below, which is freely changeable within a scope of the present invention.

<1> Compound Represented by General Formula (1) as Essential Component of Pharmaceutical Composition of the Present Invention The pharmaceutical composition of the present invention has such a feature that the compound represented by the general formula (1), such as luliconazole, is usually contained by 0.5 to 15% by mass and preferably 1 to 10% by mass. A method for producing such a component is already known (for example, Japanese Patent Application Laid-open No. 09-100279). Luliconazole is excellent in the crystallization property or crystallization performance. Crystals are deposited in some cases when luliconazole is contained by not less than 4% by mass in the case of the storage at a low temperature, for example, 5° C. depending on the type of the used solvent, even in such a state that hydroxy carboxylic acid such as lactic acid or the like is added to suppress the crystallization. In the present invention, the deposition as described above is suppressed in a combination of the medicament preparation containing the polyhydric alcohol derivative as described later on so that the biological usefulness is enhanced, especially the transfer into the nail is enhanced, and thus the treatment effect on the trichophytosis unguium is enhanced. In the case of the ordinary mycosis (fungal disease) of the foot (leg) or the mycosis of the body, a sufficient effect is provided by the compound represented by the general formula (1) by means of a treatment with a composition having a concentration of about 1 to 5% by mass. However, in the case of the mycosis of the nail such as the trichophytosis unguium or the like, it is necessary to perform a treatment with the pharmaceutical composition containing the compound represented by the general formula (1) at a concentration of 5% by mass or more. In other words, the nail is an organ or portion in which it is difficult to effect the transfer into the tissue. In order to transfer an effective amount, the content is preferably not less than 5% by mass and more preferably not less than 6% by mass. Further, it is preferable that the content is not more than 10% by mass which is the upper limit of the suppression of the crystal deposition at the low temperature. In view of the above, it is preferable that the content of the compound represented by the general formula (1) in the pharmaceutical composition for the nail is about 6 to 10% by mass.

Other than luliconazole, the compound represented by the general formula (1) is especially preferably exemplified by lanoconazole. The preferred content of lanoconazole is in conformity with the case of luliconazole as well. The salt is not specifically limited, provided that the salt is pharmaceutically acceptable. It is especially preferable to use salt of mineral acid such as salt of phosphoric acid (phosphate) or the like and salt of α-hydroxy acid such as glycolic acid, lactic acid or the like.

<2> Polyhydric Alcohol Derivative as Essential Component of Pharmaceutical Composition of the Present Invention The pharmaceutical composition of the present invention has such a feature that the polyhydric alcohol derivative is contained. Such a derivative is exemplified by the oxolane derivative (dehydrated compound of diol or cyclic acetal compound), acylated polyhydric alcohol, and etherified polyhydric alcohol. It is possible to use any one of them. Polyhydric alcohol may be preferably exemplified, for example, by glycerol, (poly)ethylene glycol, and (poly)propylene glycol.

The oxolane derivative may be preferably exemplified, for example, by the compound represented by the general formula (2). In the general formula (2), $R_3$, $R_4$, $R_5$, $R_6$ independently represent hydrogen atom, oxygen atom, carboxyl group, hydroxyalkyl group having a number of carbon atom or atoms of 1 to 4, or alkyl group having a number of carbon atom or atoms of 1 to 4, and $R_3$, $R_4$ and/or $R_5$, $R_6$ may represent the same atom together. In the case of the same atom as described above, it is preferable that the atomic species is oxygen. X represents carbon atom to which hydrogen atom is bonded or oxygen atom. X is especially preferably oxygen. Bond indicated by a broken line may be either present or absent. $R_6$ is absent when the bond indicated by the broken line is present. However, propylene carbonate is excluded.

It is preferable that the derivative is in a liquid state under a condition of 1 atmosphere (atm) at 25° C.

Specified compounds of the oxolane derivative may be preferably exemplified, for example, by tetrahydrofuran, 2-methyltetrahydrofuran, 1,3-dioxolane, 2,2-dimethyl-1,3-dioxolane, 2-oxo-1,3-dioxolane, 5-oxotetrahydrofuran-2-carboxylic acid, γ-crotonolactone, and 2,2-dimethyl-1,3-dioxolane-4-methanol. The oxolane derivative is especially preferably selected from tetrahydrofuran, 1,3-dioxolane, 5-oxotetrahydrofuran-2-carboxylic acid, and 2,2-dimethyl-1,3-dioxolane-4-methanol.

One of the derivative as described above can be used, or two or more of the derivatives as described above can be used in combination.

As for the acylated polyhydric alcohol, it is preferable to select, for example, ethylene glycol, polyethylene glycol, glycerol, polyglycerol, propylene glycol, polypropylene glycol, and 1,3-butanediol as the polyhydric alcohol base material to introduce short chain or middle chain carboxylic acid residue including, for example, acetyl group, caprylic acid residue, capric acid residue, and octanoic acid residue, or long chain fatty acid residue including, for example, lauric acid residue and oleic acid residue. The short chain fatty acid herein means those having a number of carbon atom or atoms of, for example, 1 to 4, the middle chain fatty acid means those having a number of carbon atom or atoms of, for example, 5 to 11, and the long chain fatty acid means those having a number of carbon atom or atoms of, for example, 12 to 30. The fatty acid residue preferably has a number of carbon atoms of not less than 3. The unsaturated bond may be either present or absent in the fatty acid residue. The acylated polyhydric alcohol especially preferably has the fluidity at 1 atm at 25° C.

The polymerization degrees of polyethylene glycol and polypropylene glycol are preferably about 5 to 300. The polymerization degree of polyglycerol is preferably about 2 to 20.

Specifically, the acylated polyhydric alcohol is preferably exemplified, for example, by triacetin, tricaprilin, glycerol trioctanoate, glycerol tri(caprylate/caprate), ethylene glycol monoacetate, polyethylene glycol monolaurate, polyethylene glycol monooleate, ethylene glycol diacetate, polyethylene glycol dilaurate, polyethylene glycol dioleate, and ethylene glycol diacetate. It is especially preferable to use the compound selected from triacetin, tricaprilin, glycerol trioctanoate, glycerol tri(caprylate/caprate), ethylene glycol monoacetate, polyethylene glycol monolaurate, and polyethylene glycol monooleate.

One of the derivative as described above can be used, or two or more of the derivatives as described above can be used in combination.

As for the etherified polyhydric alcohol, it is preferable to select, for example, polyethylene glycol, polyoxyethylene polymer, and polyoxyethylene-polyoxypropylene copolymer as the polyhydric alcohol base material to form an ether, for example, with alkyl group having a number of carbon atom or atoms of 1 to 20 or alkyl group which may be substituted with aromatic group. Phenyl group is preferred as the aromatic group. The etherified polyhydric alcohol especially preferably has the fluidity at 1 atm at 25° C.

The polymerization degrees of polyethylene glycol (polyoxyethylene polymer) and polyoxyethylene-polyoxypropylene copolymer are preferably about 2 to 20.

Specifically, the etherified polyhydric alcohol is preferably exemplified, for example, by diethylene glycol monoethyl ether, diethylene glycol monobenzyl ether, diethylene glycol diethyl ether, triethylene glycol dimethyl ether, polyethylene glycol lauryl ether (polyoxyethylene lauryl ether), polyoxyethylene cetyl ether, and polyoxyethylene-polyoxypropylene cetyl ether. It is especially preferable to use the compound selected from diethylene glycol monoethyl ether, diethylene glycol diethyl ether, and polyethylene glycol lauryl ether.

One of the derivative as described above can be used, or two or more of the derivatives as described above can be used in combination.

The component as described above is excellent in the function or action to solubilize the compound represented by the general formula (1), and the component as described above has the function or action to inhibit the formation of stereoisomer in a solution state. In order to express the function or action as described above, one or two or more of the compound or compounds selected from the polyhydric alcohol derivative as described above is/are preferably contained by 0.1 to 50% by mass, more preferably 1 to 20% by mass, and much more preferably 2 to 10% by mass with respect to the total amount of the pharmaceutical composition. The mass as described above is preferably ½ to 20 times the mass and more preferably 1 to 10 times the mass of the compound represented by the general formula (1).

<3> Pharmaceutical Composition of the Present Invention

The pharmaceutical composition of the present invention has such a feature that the essential components as described above are contained and arbitrary components are contained in order to prepare or formulate the medicament preparation (pharmaceutical preparation). The arbitrary components, which are used to prepare or formulate the medicament preparation, are preferably exemplified, for example, by alcohols including, for example, ethanol and isopropanol; ketones including, for example, acetone; nonionic surfactants including, for example, polyoxyethylene cured castor oil and polyoxyethylene sorbitan fatty acid; hydroxypropyl cellulose, ethylcellulose, and higher alcohols such as isostearyl alcohol, oleyl alcohol and the like; polyhydric alcohols including, for example, propylene glycol; diesters of dibasic acids including, for example, diethyl sebacate, dipropyl sebacate, and diethyl adipate; hydroxyalkylbenzene including, for example, benzyl alcohol, phenethyl alcohol, and phenyl propanol; stabilizers or stabilizing agents including, for example, α-hydroxy acids such as lactic acid, glycolic acid, citric acid and the like and mineral acids such as phosphoric acid and the like; and solvents including, for example, alkylene carbonate such as propylene carbonate and the like, N-methyl-2-pyrrolidone (hereinafter referred to as "NMP"), and crotamiton. Among them, hydroxyalkylbenzene, and the stabilizer, which is exemplified, for example, by α-hydroxy acid, and phosphoric acid, act together with the polyhydric alcohol derivative to exhibit the excellent solubilization performance for the compound represented by the general formula (1) and/or the salt thereof and the action to suppress the formation of stereoisomer. Therefore, it is especially preferable to contain a combination of such compounds.

The alkyl group, which has a number of carbon atom or atoms of 1 to 4, is preferred in relation to the hydroxyalkylbenzene. Specifically, there are preferably exemplified, for example, benzyl alcohol, phenethyl alcohol, and phenylpropanol. Only one species of the component as described above may be contained, or two or more species may be contained in combination. Benzyl alcohol or phenethyl alcohol is especially preferred. More preferably, benzyl alcohol is used. The component as described above is preferably contained by 5 to 99% by mass in a total amount and more preferably 10 to 99% by mass with respect to the total amount of the pharmaceutical composition. When the component or components as described above is/are contained in the content as described above, the function or action, in which the solubilized state is stabilized and the crystal deposition is avoided, is exhibited during the storage of the compound represented by the general formula (1) and/or the salt thereof in the low temperature region, for example, in the vicinity of 5° C. Further, as for the stability at a high temperature of not less than 40° C., the function or action, in which the formation of stereoisomer of the compound represented by the general formula (1) is suppressed, is provided. In particular, the crystal deposition is suppressed in the low temperature region. Therefore, it is preferable to use the component or components as described above as the dissolution auxiliary agent for the compound represented by the general formula (1) and/or the salt thereof. That is, the production is preferably performed as follows.

The compound represented by the general formula (1) and/or the salt thereof is/are wetted or immersed (infiltrated) with hydroxyalkylbenzene, followed by being agitated (stirred) and solubilized, with being heated in order to effect the solubilization, if desired. After that, the polyhydric alcohol derivative is added thereto, so as to dilute a mixture and to cause the solvation. After that, the remaining solvent is added thereto, followed by being heated, if desired, agitated (stirred), and solubilized.

In the present invention, the means for replacing propylene carbonate, N-methyl-2-pyrrolidone, and crotamiton can be provided by using the polyhydric alcohol derivative or combining the polyhydric alcohol derivative and hydroxyalkylbenzene such as benzyl alcohol or the like. Therefore, the medicament preparation can be prepared or formulated without using propylene carbonate, N-methyl-2-pyrrolidone, and crotamiton. However, it is also preferable to provide the medicament preparation with using the compounds as described above in view of the supplementation for the technique. The medicament preparation, in which the compounds as described above are used, also belongs to the technical scope of the present invention. When alkylene carbonate such as propylene carbonate or the like, NMP, or crotamiton is contained, the component can be contained preferably by 1 to 30% by mass and more preferably 2 to 15% by mass with respect to the total amount of the pharmaceutical composition.

Further, in order to improve the stability of the pharmaceutical composition of the present invention and the effect to suppress the crystal deposition after the application, it is also preferable to contain the stabilizer or stabilizing agent including, for example, α-hydroxy acids such as lactic acid, glycolic acid, citric acid and the like and mineral acids such as phosphoric acid and the like by 0.1 to 20% by mass, more preferably 1 to 10% by mass with respect to the total amount of the pharmaceutical composition. Additionally, in order to improve the solubilizing performance (solubility) and the stability, it is also preferable to contain higher alcohol such as isostearyl alcohol or the like which is in a form of liquid at 1 atm at 25° C. by 10 to 30% by mass, more preferably 15 to 25% by mass. Additionally, in order to improve the solubilizing performance (solubility), it is also preferable to contain polyhydric alcohol such as propylene glycol by 1 to 30% by mass, more preferably 5 to 20% by mass with respect to the total amount of the pharmaceutical composition.

The pharmaceutical composition of the present invention can be produced by treating the essential components and the arbitrary components as described above in accordance with the ordinary method.

As for the pharmaceutical composition of the present invention, any agent form, which is used in the pharmaceutical composition, can be applied without any special limitation. There are exemplified, for example, the oral administration medicament preparation including, for example, the tablet or pill, the capsule, the granule, the film coating agent, the powder, and the syrup; and the non-oral administration medicament including, for example, the injection, the suppository, the inhalant or inhalation, the embrocation or liniment, the patch, the aerosol, the percutaneous absorbent, the eye drop or eye lotion, and the nose drop. In particular, it is possible to preferably exemplify the skin external preparation including, for example, the embrocation or liniment, the patch, the aerosol, and the percutaneous absorbent. The form of the skin external preparation is preferably exemplified, for example, by the lotion, the emulsion or emulsified lotion, the gel, the cream, the aerosol, the nail enamel, and the hydrogel patch. The lotion is especially preferred.

The pharmaceutical composition of the present invention is preferably used to treat the disease caused by the fungus or the prevention of the deterioration of the disease by utilizing the characteristics of the luliconazole and the like. The disease caused by the fungus is exemplified by the foot trichophytosis such as the athlete's foot or dermatophytosis, the body trichophytosis such as the candida or candidosis and the pityriasis versicolor, and the trichophytosis at the hard keratin portion such as the trichophytosis unguium. The pharmaceutical composition of the present invention is especially preferably used to treat the hard keratin portion such as the trichophytosis unguium, because the effect is especially remarkable. The effect of the pharmaceutical composition of the present invention is especially preferably expressed on the nail. However, the effect is also exerted on the ordinary skin mycosis or fungal disease. Therefore, the pharmaceutical composition, which is directed to the skin mycosis or fungal disease and which satisfies the requirement of the present invention, also belongs to the technical scope of the present invention. The skin mycosis as described above can be exemplified, for example, by the foot trichophytosis and the keratin proliferation type trichophytosis which appears, for example, on the heel and which is included in the foot trichophytosis. In the skin mycosis as described above, the present invention is preferably applied to the keratin proliferation type trichophytosis on which any effect is hardly obtained by any ordinary medicament (agent or drug), because the effect of the present invention remarkably appears thereon.

The mode of use can be appropriately selected by considering, for example, the weight, the age, the sex, and the disease condition of the patient. However, in the case of the ordinary adult, it is preferable to administrate 0.01 to 1 g per day of the compound represented by the general formula (1) and/or the salt thereof. It is possible to make reference to the amount of use of the compound represented by the general formula (1) and/or the salt thereof ordinarily used for the disease caused by the fungus.

For example, in the case of the external preparation, it is possible to exemplify the application of an appropriate amount to the disease portion once or several times a day. It is preferable that such a treatment is performed every day. In particular, in the case of the trichophytosis unguium, for example, luliconazole and the like as the active ingredient can be transferred into the nail in an amount which cannot be achieved with any ordinary medicament preparation. Accordingly, the trichophytosis unguium can be treated by means of only the external application without internally taking the antimycotic agent (drug) for a long period of time. Further, in the case of the trichophytosis unguium, a serious problem arises in relation to the recrudesce and the reinfection. However, it is possible to avoid the recrudesce and the reinfection as described above by administering the pharmaceutical composition of the present invention for 1 to 2 weeks after the sedation of the disease condition. In the form as described above, the pharmaceutical composition of the present invention provides the preventive effect.

EXAMPLES

The present invention will be explained in further detail below as exemplified by Examples. However, the present invention is not limited to Examples described below.

Example 1

Pharmaceutical compositions of the present invention were produced in accordance with the following formulations. That is, luliconazole was added to lactic acid and benzyl alcohol and dissolved. If luliconazole was not dissolved, the mixture was heated to dissolve luliconazole. After that, the mixture was diluted with a polyhydric alcohol derivative, and other components were successively added, followed by being homogeneously agitated to produce each of pharmaceutical compositions 1 to 10 of the present invention. Comparative Example 1 was also prepared by performing the process in the same manner as described above. The preparations were stored for 3 weeks at 60° C. The amounts of SE isomer and Z isomer produced as the stereoisomers of luliconazole were quantitatively measured under the following HPLC (high performance liquid chromatography) condition.

The structures of SE isomer and Z isomer as the stereoisomers of luliconazole are shown below.

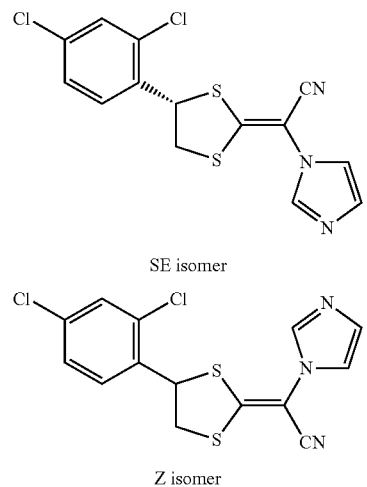

<High Performance Liquid Chromatography Condition>

Column: optically active column CHIRALCEL OD-RH 4.6×150 mm;

Mobile phase: aqueous sodium perchlorate solution: methanol=80:20→60:40 (linear gradient);

Flow rate: 0.5 ml/min.;

Column temperature: 40° C.;

Detection wavelength: 275 nm.

Results are shown in Table 1. According to Table 1, it is shown that the acylated derivative of polyhydric alcohol has the action which is the same as or equivalent to those of propylene carbonate, N-methyl-2-pyrrolidone (NMP) and crotamiton.

TABLE 1

|  | Formulation (g) (Composition No.) | | | | | | | | | | Comp. Ex. (g) |
| --- | --- | --- | --- | --- | --- | --- | --- | --- | --- | --- | --- |
|  | 1 | 2 | 3 | 4 | 5 | 6 | 7 | 8 | 9 | 10 | 1 |
| Luliconazole | 1 | 1 | 1 | 1 | 1 | 1 | 1 | 8 | 8 | 8 | 1 |
| Triacetin | 10 | | | | | | | | | | |

TABLE 1-continued

|  | Formulation (g) (Composition No.) | | | | | | | | | | Comp. Ex. (g) |
|---|---|---|---|---|---|---|---|---|---|---|---|
|  | 1 | 2 | 3 | 4 | 5 | 6 | 7 | 8 | 9 | 10 | 1 |
| Tricaprilin |  | 10 |  |  |  |  |  |  |  |  |  |
| Glycerol tri(caprylate/caprate) (Triester F-810) |  |  | 10 |  |  |  |  |  |  |  |  |
| Glycerol triisooctanate (Trifat S308) |  |  |  | 10 |  |  |  |  |  |  |  |
| 2-Hydroxyethyl acetate (ethylene glycol monoacetate) |  |  |  |  | 10 |  |  | 10 |  |  |  |
| Polyethylene glycol monolaurate (MYL-10) |  |  |  |  |  | 10 |  |  | 10 |  |  |
| Polyethylene glycol monooleate (MYO-10) |  |  |  |  |  |  | 10 |  |  | 10 |  |
| Lactic acid | 1 | 1 | 1 | 1 | 1 | 1 | 1 | 6 | 6 | 6 |  |
| Benzyl alcohol | 1 | 1 | 1 | 1 | 1 | 1 | 1 | 2 | 2 | 2 |  |
| Propylene carbonate |  |  |  |  |  |  |  | 5 | 5 | 5 |  |
| Acetone |  |  |  |  |  |  |  |  |  |  |  |
| Propylene glycol |  |  |  |  |  |  |  | 10 | 10 | 10 |  |
| Anhydrous ethanol | 87 | 87 | 87 | 87 | 87 | 87 | 87 | 59 | 59 | 59 | 99 |
| Total | 100 | 100 | 100 | 100 | 100 | 100 | 100 | 100 | 100 | 100 | 100 |
| Production | ○ | ○ | ○ | ○ | ○ | ○ | ○ | ○ | ○ | ○ | ○ |
| Presence or absence of deposition |  |  |  |  |  |  |  |  |  |  |  |
| Upon start | ○ | ○ | ○ | ○ | ○ | ○ | ○ | ○ | ○ | ○ | ○ |
| 5° C., 3 days | ○ | ○ | ○ | ○ | ○ | ○ | ○ | ○ | ○ | ○ | ○ |
| 5° C., 1 week | ○ | ○ | ○ | ○ | ○ | ○ | ○ | ○ | ○ | ○ | ○ |
| 5° C., 1 month | ○ | ○ | ○ | ○ | ○ | ○ | ○ | ○ | ○ | ○ | ○ |
| (60° C., 3 weeks) | ○ | ○ | ○ | ○ | ○ | ○ | ○ | ○ | ○ | ○ | ○ |
| Stability |  |  |  |  |  |  |  |  |  |  |  |
| Upon start |  |  |  |  |  |  |  |  |  |  |  |
| Purity SE isomer (%) | 0.23 | 0.24 | 0.22 | 0.23 | 0.22 | 0.24 | 0.21 | 0.24 | 0.23 | 0.24 | 0.31 |
| Z isomer (%) | 0.03 | 0.03 | 0.03 | 0.03 | 0.03 | 0.02 | 0.03 | 0.02 | 0.03 | 0.02 | 0.03 |
| Others (%) | 0.01 | 0.01 | 0.01 | 0.00 | 0.01 | 0.01 | 0.00 | 0.00 | 0.00 | 0.01 | 0.00 |
| 60° C., 3 weeks |  |  |  |  |  |  |  |  |  |  |  |
| Purity SE isomer (%) | 0.23 | 0.23 | 0.24 | 0.25 | 0.22 | 0.26 | 0.27 | 0.27 | 0.28 | 0.28 | 32.66 |
| Z isomer (%) | 0.06 | 0.04 | 0.05 | 0.05 | 0.07 | 0.07 | 0.1 | 0.08 | 0.09 | 0.11 | 2.64 |
| Others (%) | 0.01 | 0.04 | 0.01 | 0.02 | 0.01 | 0.05 | 0.11 | 0.2 | 0.2 | 0.25 | 0.18 |

○ in Production: Uniform solution was obtained
○ in Deposition: No deposition

Example 2

Pharmaceutical compositions 11 to 20 were prepared in accordance with the following formulations in the same manner as in Example 1. Comparative Example 2 was also prepared in accordance with the same or equivalent process.

Results are shown in Table 2. It is shown that the pharmaceutical composition of the present invention has the excellent solubilizing performance (solubility) and the excellent stabilizing action even in the case of the use of the oxolane derivative of polyhydric alcohol corresponding to the cyclic acetal compound or the dehydrated compound of diol.

TABLE 2

|  | Formulation (g) (Composition No.) | | | | | | | | | | Comp. Ex. (g) |
|---|---|---|---|---|---|---|---|---|---|---|---|
|  | 11 | 12 | 13 | 14 | 15 | 16 | 17 | 18 | 19 | 20 | 2 |
| Luliconazole | 1 | 1 | 1 | 1 | 10 | 15 | 10 | 8 | 1 | 1 | 1 |
| Tetrahydrofuran | 10 |  |  |  |  |  |  |  |  |  |  |
| 1,3-Dioxolane |  | 10 |  |  | 10 | 10 | 5 |  |  |  |  |
| 2-Oxo-1,3-dioxolane |  |  |  |  |  |  |  | 10 | 10 |  |  |
| (s)-(+)-5-Oxotetrahydrofuran-2-carboxylic acid |  |  |  | 10 |  |  |  |  |  |  |  |
| γ-Crotonolactone |  |  |  |  |  |  |  |  |  | 10 |  |
| 2,2-Dimethyl-1,3-dioxolane-4-methanol |  |  | 10 |  |  |  |  |  |  |  |  |
| Lactic acid | 1 | 1 | 1 | 1 | 8 | 8 | 8 | 6 | 1 | 1 |  |
| Benzyl alcohol | 1 | 1 | 1 | 1 | 2 | 4 | 2 | 2 | 1 | 1 |  |
| Propylene carbonate |  |  |  |  | 5 | 5 |  | 5 |  |  |  |
| Acetone |  |  |  |  |  |  | 10 |  |  |  |  |
| Propylene glycol |  |  |  |  | 10 | 15 | 10 | 10 |  |  |  |
| Anhydrous ethanol | 87 | 87 | 87 | 87 | 55 | 43 | 55 | 59 | 87 | 87 | 99 |
| Total | 100 | 100 | 100 | 100 | 100 | 100 | 100 | 100 | 100 | 100 | 100 |
| Production | ○ | ○ | ○ | ○ | ○ | ○ | ○ | ○ | ○ | ○ | ○ |

TABLE 2-continued

|  | Formulation (g) (Composition No.) | | | | | | | | | | Comp. Ex. (g) |
|---|---|---|---|---|---|---|---|---|---|---|---|
|  | 11 | 12 | 13 | 14 | 15 | 16 | 17 | 18 | 19 | 20 | 2 |
| Presence or absence of deposition | | | | | | | | | | | |
| Upon start | ○ | ○ | ○ | ○ | ○ | ○ | ○ | ○ | ○ | ○ | ○ |
| 5° C., 3 days | ○ | ○ | ○ | ○ | ○ | ○ | ○ | ○ | ○ | ○ | ○ |
| 5° C., 1 week | ○ | ○ | ○ | ○ | ○ | ○ | ○ | ○ | ○ | ○ | ○ |
| 5° C., 1 month | ○ | ○ | ○ | ○ | ○ | ○ | ○ | ○ | ○ | ○ | ○ |
| (60° C., 3 weeks) | ○ | ○ | ○ | ○ | ○ | ○ | ○ | ○ | ○ | ○ | ○ |
| Stability | | | | | | | | | | | |
| Upon start | | | | | | | | | | | |
| Purity SE isomer (%) | 0.24 | 0.24 | 0.25 | 0.24 | 0.24 | 0.24 | 0.23 | 0.23 | 0.25 | 0.25 | 0.31 |
| Z isomer (%) | 0.03 | 0.03 | 0.03 | 0.03 | 0.03 | 0.03 | 0.03 | 0.03 | 0.03 | 0.03 | 0.03 |
| Others (%) | 0.00 | 0.00 | 0.02 | 0.01 | 0.00 | 0.00 | 0.00 | 0.00 | 0.00 | 0.02 | 0.00 |
| 60° C., 3 weeks | | | | | | | | | | | |
| Purity SE isomer (%) | 0.23 | 0.24 | 0.26 | 0.24 | 0.27 | 0.26 | 0.26 | 0.28 | 0.26 | 0.23 | 32.66 |
| Z isomer (%) | 0.06 | 0.06 | 0.05 | 0.06 | 0.08 | 0.1 | 0.08 | 0.14 | 0.09 | 0.07 | 2.64 |
| Others (%) | 0.00 | 0.02 | 0.16 | 0.14 | 0.27 | 0.25 | 0.08 | 4.98 | 4.18 | 6.03 | 0.18 |

○ in Production: Uniform solution was obtained
○ in Deposition: No deposition

Example 3

Pharmaceutical compositions 21 to 33 were prepared in accordance with the following formulations in the same manner as in Example 1. Comparative Example 3 was also prepared in accordance with the same or equivalent process.

Results are shown in Table 3. It is shown that the pharmaceutical composition of the present invention has the excellent solubilizing performance (solubility) and the excellent stabilizing action even in the case of the use of the etherified derivative of the polyhydric alcohol.

TABLE 3

|  | Formulation (g) (Composition No.) | | | | | | | | | | | | | Comp. Ex. (g) |
|---|---|---|---|---|---|---|---|---|---|---|---|---|---|---|
|  | 21 | 22 | 23 | 24 | 25 | 26 | 27 | 28 | 29 | 30 | 31 | 32 | 33 | 3 |
| Luliconazole | 1 | 1 | 1 | 1 | 1 | 5 | 5 | 5 | 5 | 5 | 5 | 5 | 5 | 1 |
| Diethylene glycol | 10 | | | | | | 10 | 10 | 10 | | | | | |
| Diethylene glycol monoethyl ether | | | | | | | | | | 10 | | | | |
| Diethylene glycol monobenzyl ether | | 10 | | | | | | | | | | | | |
| Diethylene glycol diethyl ether | | | 10 | | | 10 | | | | | 10 | | | |
| Triethylene glycol | | | | 10 | | | | | | | | 10 | | |
| Triethylene glycol dimethyl ether | | | | | 10 | | | | | | | | 10 | |
| Polyoxyethylene lauryl ether (BL-42) | | | | | | | 5 | | | 5 | 5 | 5 | 5 | |
| Polyoxyethylene cetyl ether (BC-10) | | | | | | | | 5 | | | | | | |
| Polyoxyethylene (10) polyoxypropylene (4) cetyl ether (PBC-33) | | | | | | | | | 5 | | | | | |
| Lactic acid | 1 | 1 | 1 | 1 | 1 | 4 | 4 | 4 | 4 | 4 | 4 | 4 | 4 | |
| Benzyl alcohol | 1 | 1 | 1 | 1 | 1 | 2 | 2 | 2 | 2 | 2 | 2 | 2 | 2 | |
| Propylene carbonate | | | | | | 5 | 5 | 5 | 5 | 5 | 5 | 5 | 5 | |
| Anhydrous ethanol | 87 | 87 | 87 | 87 | 87 | 74 | 69 | 69 | 69 | 69 | 69 | 69 | 69 | 99 |
| Total | 100 | 100 | 100 | 100 | 100 | 100 | 100 | 100 | 100 | 100 | 100 | 100 | 100 | 100 |
| Production | ○ | ○ | ○ | ○ | ○ | ○ | ○ | ○ | ○ | ○ | ○ | ○ | ○ | ○ |

TABLE 3-continued

| | Formulation (g) (Composition No.) | | | | | | | | | | | | | Comp. Ex. (g) |
|---|---|---|---|---|---|---|---|---|---|---|---|---|---|---|
| | 21 | 22 | 23 | 24 | 25 | 26 | 27 | 28 | 29 | 30 | 31 | 32 | 33 | 3 |
| Presence or absence of deposition | | | | | | | | | | | | | | |
| Upon start | ○ | ○ | ○ | ○ | ○ | ○ | ○ | ○ | ○ | ○ | ○ | ○ | ○ | ○ |
| 5° C., 3 days | ○ | ○ | ○ | ○ | ○ | ○ | ○ | ○ | ○ | ○ | ○ | ○ | ○ | ○ |
| 5° C., 1 week | ○ | ○ | ○ | ○ | ○ | ○ | ○ | ○ | ○ | ○ | ○ | ○ | ○ | ○ |
| 5° C., 1 month | ○ | ○ | ○ | ○ | ○ | ○ | ○ | ○ | ○ | ○ | ○ | ○ | ○ | ○ |
| (60° C., 3 weeks) | ○ | ○ | ○ | ○ | ○ | ○ | ○ | ○ | ○ | ○ | ○ | ○ | ○ | ○ |
| Stability | | | | | | | | | | | | | | |
| Upon start | | | | | | | | | | | | | | |
| Purity SE isomer (%) | 0.24 | 0.24 | 0.22 | 0.22 | 0.22 | 0.21 | 0.23 | 0.22 | 0.22 | 0.21 | 0.22 | 0.22 | 0.21 | 0.31 |
| Z isomer (%) | 0.03 | 0.03 | 0.03 | 0.03 | 0.03 | 0.03 | 0.02 | 0.03 | 0.02 | 0.02 | 0.02 | 0.02 | 0.02 | 0.03 |
| Others (%) | 0.00 | 0.00 | 0.00 | 0.00 | 0.00 | 0.00 | 0.01 | 0.00 | 0.00 | 0.00 | 0.00 | 0.01 | 0.00 | 0.00 |
| 60° C., 3 weeks | | | | | | | | | | | | | | |
| Purity SE isomer (%) | 0.25 | 0.24 | 0.23 | 0.26 | 0.24 | 0.27 | 0.26 | 0.25 | 0.25 | 0.25 | 0.25 | 0.26 | 0.26 | 32.66 |
| Z isomer (%) | 0.06 | 0.06 | 0.07 | 0.08 | 0.06 | 0.07 | 0.09 | 0.10 | 0.09 | 0.08 | 0.07 | 0.09 | 0.08 | 2.64 |
| Others (%) | 0.01 | 0.05 | 0.01 | 0.01 | 0.01 | 0.14 | 0.19 | 0.21 | 0.18 | 0.17 | 0.16 | 0.18 | 0.17 | 0.18 |

○ in Production: Uniform solution was obtained
○ in Deposition: No deposition

INDUSTRIAL APPLICABILITY

The present invention is applicable to the pharmaceutical composition.

What is claimed is:
1. A pharmaceutical composition consisting of:
   1) from 6 to 15% compound represented by the following general formula (1)

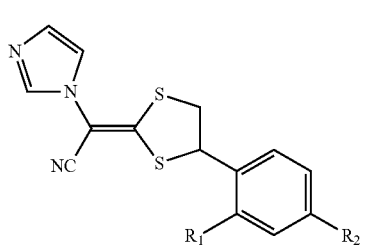

General formula (1)

and/or salt thereof;
   2) from 2 to 10% one or more etherified compound of polyhydric alcohol derivative selected from the group consisting of diethylene glycol diethyl ether, and triethylene glycol dimethyl ether;
   3) from 1 to 10% α-hydroxy acid and/or phosphoric acid; and
   4) from 59 to 87% ethanol;
   5) hydroxyalkylbenzene; and
   6) Propylene carbonate,
   wherein concentrations are percentages by mass based on the total amount of the pharmaceutical composition:
   and wherein, in the formula (1), R1, R2 independently represent hydrogen atom or halogen atom respectively, and at least one of R1, R2 is halogen atom.

2. The pharmaceutical composition according to claim 1, wherein the compound represented by the general formula (I) is luliconazole and wherein R1=R2=chlorine atom.

3. The pharmaceutical composition according to claim 1, wherein the hydroxyalkylbenzene is benzyl alcohol.

4. The pharmaceutical composition according to claim 1, wherein the α-hydroxy acid is lactic acid.

5. A method for producing a pharmaceutical composition of claim 1 consisting of:
   1) from 6 to 15% compound represented by the following general formula (1)

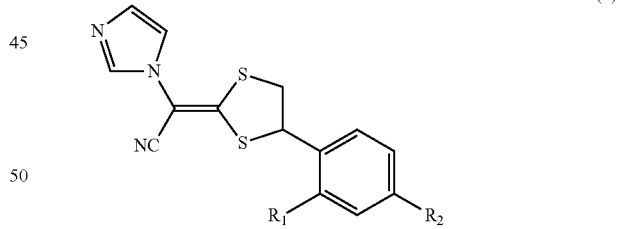

General formula (1)

and/or salt thereof;
   2) from 2 to 10% one or more etherified compound of polyhydric alcohol derivative selected from the group consisting of diethylene glycol diethyl ether, and triethylene glycol dimethyl ether;
   3) from 1 to 10% α-hydroxy acid and/or phosphoric acid;
   4) from 59 to 87% ethanol;
   5) hydroxyalkylbenzene; and
   6) Propylene carbonate,
   wherein concentrations are percentages by mass based on the total amount of the pharmaceutical composition,
   the method comprising:
   first mixing step: mixing hydroxyalkylbenzene propylene carbonate and α-hydroxy acid and/or phosphoric acid with the compound represented by the general formula (1) and/or the salt thereof in ethanol; and second mixing step: mixing an obtained mixture with the polyhydric alcohol derivative:

wherein, in the formula (1), $R_1$, $R_2$ independently represent hydrogen atom or halogen atom respectively, and at least one of $R_1$, $R_2$ is halogen atom.

6. The pharmaceutical composition according to claim 2, wherein the α-hydroxy acid is lactic acid.

7. The method for producing a pharmaceutical composition according to claim 5, wherein the hydroxyalkylbenzene is benzyl alcohol.

8. The pharmaceutical composition according to claim 1 obtainable by the method comprising:

first mixing step: mixing hydroxyalkylbenzene propylene carbonate and α-hydroxy acid and/or phosphoric acid with the compound represented by the general formula (1) and/or the salt thereof in ethanol; and second mixing step: mixing an obtained mixture with the polyhydric alcohol derivative.

* * * * *